(12) United States Patent
Dinh

(10) Patent No.: US 8,974,368 B2
(45) Date of Patent: Mar. 10, 2015

(54) PELVIC TISSUE SUPPORT DEVICES

(75) Inventor: Thomas Q. Dinh, Minnetonka, MN (US)

(73) Assignee: AMS Research Corporation, Minnetonka, MN (US)

( * ) Notice: Subject to any disclaimer, the term of this patent is extended or adjusted under 35 U.S.C. 154(b) by 290 days.

(21) Appl. No.: 13/265,723

(22) PCT Filed: Apr. 28, 2010

(86) PCT No.: PCT/US2010/032746
§ 371 (c)(1),
(2), (4) Date: Oct. 21, 2011

(87) PCT Pub. No.: WO2010/129331
PCT Pub. Date: Nov. 11, 2010

(65) Prior Publication Data
US 2012/0041418 A1     Feb. 16, 2012

(51) Int. Cl.
*A61F 2/02*     (2006.01)
*A61L 31/16*    (2006.01)
*A61K 9/00*     (2006.01)
*A61L 31/14*    (2006.01)

(52) U.S. Cl.
CPC ............... *A61L 31/16* (2013.01); *A61K 9/0019* (2013.01); *A61K 9/0034* (2013.01); *A61L 31/148* (2013.01); *A61L 2300/00* (2013.01); *A61L 2400/06* (2013.01)
USPC .............................. 600/37; 606/151; 424/572

(58) Field of Classification Search
None
See application file for complete search history.

(56) References Cited

U.S. PATENT DOCUMENTS

| 5,880,108 A * | 3/1999 | Morales et al. ................. 514/54 |
| 6,933,326 B1 | 8/2005 | Griffey et al. |
| 2003/0130670 A1 | 7/2003 | Anderson et al. |

FOREIGN PATENT DOCUMENTS

WO     WO 98/43555 A1     10/1998

OTHER PUBLICATIONS

J Christian Winters., "InteXen tissue processing and laboratory study," International Urogynecology Journal; Including Pelvic Floor Dysfunction, Springer-Verlag, LO LNKD-DOI: 10.1007/S00192-006-0108-8, vol. 17, No. 1, May 6, 2006, pp. 34-38, XP019511595ISSN: 1433-3023.

* cited by examiner

*Primary Examiner* — Allison Fox
(74) *Attorney, Agent, or Firm* — Kagan Binder, PLLC

(57) ABSTRACT

A delivery system is provided that is adapted to treat various urological pelvic disorders, such as prolapse, incontinence, and the like. The delivery system can include at least one biologic loaded or otherwise provided with a bioactive agent. The biologic can comprise any drugs, hormones or steroids, stem cells, growth factors, proteins, and/or other bioactive agents to promote cell or tissue growth for the treatment and strengthening of organ walls or tissue. The biologic is generally adapted to controllably release the agent to the surrounding tissue or organ to provide a local and targeted delivery.

11 Claims, 3 Drawing Sheets

PELVIC TISSUE SUPPORT DEVICES

RELATED APPLICATION

This application claims the benefit from International Application No. PCT/US2010/032746, which was filed on Apr. 28, 2010, which in turns claims priority under 35 U.S.C. §119(e) to U.S. Provisional Application No. 61/173,265, filed Apr. 28, 2009, which are both incorporated herein by reference in their entireties.

FIELD OF THE INVENTION

The present invention relates generally to a treatment delivery system and method and, more specifically, to local and targeted delivery using a biologic loaded with an agent to treat prolapse, incontinence, and/or other urological disorders in males and females.

BACKGROUND OF THE INVENTION

Vaginal prolapse changes the position of the vagina, which can lead to discomfort, urinary incontinence, and incomplete emptying of the bladder. In severe cases, vaginal prolapse conditions can even cause the vagina to become positioned outside of the body.

In a normal female body, the levator ani muscles close the pelvic floor and support the vagina. This results in little force being applied to the fascia and ligaments that support the vagina. Increases in abdominal pressure, failure of the muscles to keep the pelvic floor closed, and damage to ligaments and fascia can all contribute to the development of prolapse. Because, childbirth can lessen the strength of relevant connective tissue as well as the strength of surrounding muscles, it has been implicated as causing vaginal prolapse.

However, studies have shown that a majority of prolapse cases occur years after childbirth, suggesting that factors other than injury from childbirth contribute to the disease. Indeed, menopause accounts for more instances of prolapse than injury from childbirth. This trend suggests that ovarian steroids, especially estrogen, greatly influence the strength of pelvic floor connective tissues.

In order to treat weakening after menopause, a woman may use hormone replacement therapy or vaginal estrogen cream. However, women are generally discouraged from using long-term hormone replacement therapy because of associated health risks. Vaginal estrogen cream is thought to be a lower-risk treatment than hormone replacement therapy or estrogen alone because vaginal estrogen cream is low-dose and has a localized effect. However, the vaginal estrogen cream must be manually applied by the patient as directed, e.g., daily. Additionally, the vaginal estrogen cream is messy during application and use.

Another pelvic disorder that can occur in patients is referred to as urinary incontinence or involuntary loss of urinary control, which is a problem that afflicts men, women, and children of all ages. A variety of treatment options for incontinence are currently available. Some of these include external devices, behavioral therapy (such as biofeedback, electrical stimulation, or Kegel exercises), and prosthetic devices.

Recently, crosslinked bovine collagen has been used as a bulking agent to treat incontinence with symptomatic improvement in many patients. However, more than one injection treatment session is required to achieve satisfactory results. Furthermore, crosslinked collagen causes local tissue hypersensitivity due to the chemical used to crosslink the collagen. There is a need for a bulking agent treatment that eliminates multiple injection sessions and does not cause tissue hypersensitivity.

SUMMARY OF THE INVENTION

The current invention is directed to a biologic delivery system that treats prolapse, incontinence, and/or other urological disorders in males and females. To eliminate serious problems associated with systemic therapies, the delivery system provides for low dosages, and local and targeted delivery. Additionally, the delivery system eliminates the need for repeated dosages to achieve optimal results. The delivery system generally comprises a biologic, including at least one bioactive agent.

The biologic can comprise any drug, drugs, or combination thereof to treat a specific pelvic disorder. The biologic can comprise crosslinked bovine collagen. The crosslinked bovine collagen can strengthen walls of organs to treat pelvic disorders. The biologic can comprise hormones or steroids. For example, the biologic can comprise the ovarian steroid, estrogen, to treat vaginal prolapse. Ovarian steroids can increase the thickness of the vaginal tube. The biologic can comprise other bioactive agents or growth factors. A bioactive agent can recruit cells and other growth factors to the treatment site to repair a body part in a natural way. The biologic can also include but not be limited to porcine dermis and cadaveric tissue. The biologic can be a simple formulation and, therefore, easy and inexpensive to manufacture.

The biologic can be delivered locally to the desired location within the pelvic area in order to treat a pelvic disorder, e.g., via an injection needle. Further, the biologic can be provided with known implant or pelvic tissue support devices to facilitate local delivery while mechanically supporting the structure(s) affected by the pelvic disorder. The biologic is generally adapted to controllably release the agent over time. The biologic can degrade over time, allowing the damaged tissues to remodel back into normal anatomical positions, in order to prevent future recurrent prolapse.

DETAILED DESCRIPTION OF PREFERRED EMBODIMENTS

Embodiments of the present invention are directed to a delivery system adapted to treat various urological disorders, such as prolapse, incontinence, and the like. The delivery system can include at least one biologic loaded or otherwise provided with a bioactive agent.

Figure 1:
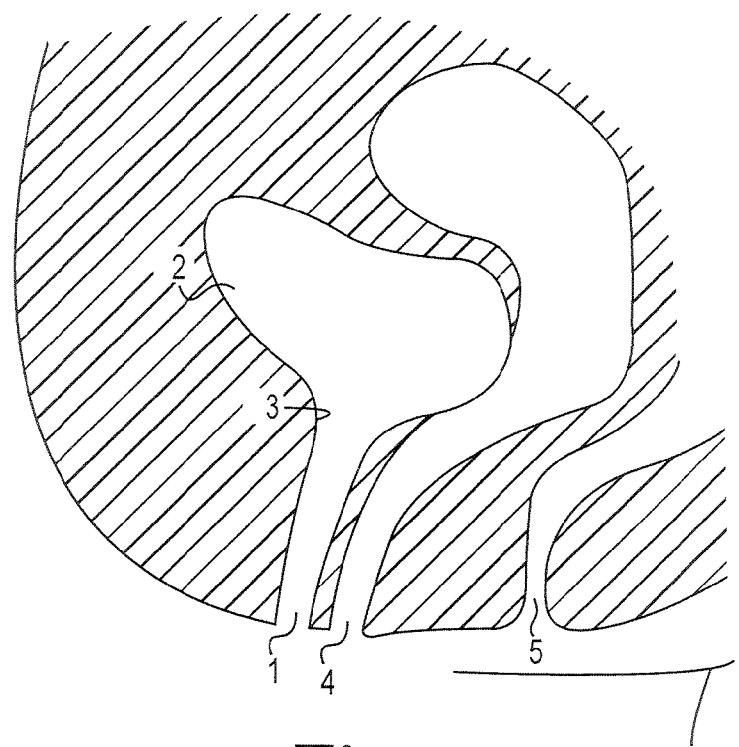
FIG. 1 schematically illustrates relevant pelvic female anatomy.
Figure 2:
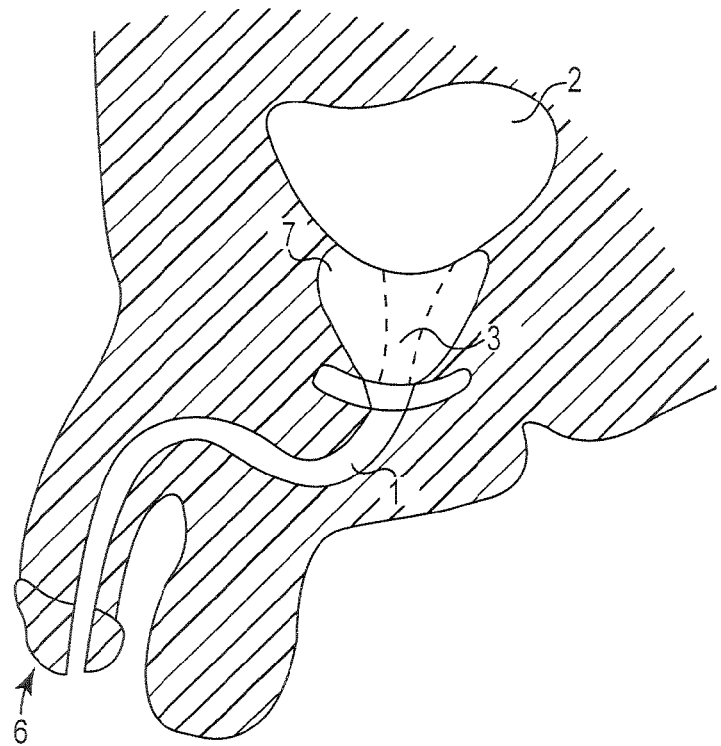
FIG. 2 schematically illustrates relevant pelvic male anatomy.

FIGS. 1-2 schematically illustrate the relevant pelvic female and male anatomy to demonstrate the potential organs or tissue that can be targeted (at or proximate) with the localized and targeted treatment of the present invention. Ligaments hold the bladder in place and connect it to the pelvic and other tissue.

As shown in FIG. 1, the female anatomy includes the urethra 1 and the bladder 2. The urethra 1 is a tube that passes urine from the bladder 2 out of the body. The narrow, internal opening of the urethra 1 within the bladder 2 is the bladder neck 3. In this region, the bladder's bundled muscular fibers transition into a sphincteric striated muscle called the internal sphincter. The vagina 4 and anus 5 are further depicted.

FIG. 2 illustrates the relevant male anatomy. The urethra 1 extends from the bladder neck 3 to the end of the penis 6. The male urethra is composed of three portions: the prostatic, bulbar and pendulous portions. The prostatic portion is the widest part of the tube, which passes through the prostate gland 7.

The biologic in accordance with embodiments of the present invention can be any known material or device adapted to deliver an agent to the desired location within the pelvic area to treat the aforementioned pelvic disorders. The biologic can comprise any drugs, hormones or steroids, stem cells, growth factors, proteins, and/or other bioactive agents known to those of ordinary skill in the art to recruit cells and promote cell or tissue growth for the treatment and strengthening of organ walls or tissue to treat pelvic disorders.

As such, the biologic is generally adapted to controllably release the agent to the surrounding tissue or organ to provide a local and targeted delivery. The biologic can degrade over time, remodeling the damaged tissue back into its normal anatomical state or position to prevent future problems or pelvic disorders.

In various embodiments, an injectable formulation of biologics can be injected around the urethra or surrounding tissue to treat incontinence and strengthen the urethral wall to prevent or treat incontinence. For instance, the delivering of proteins or growth factors to the urethra or its surrounding tissue can restore the function of the muscles around the sphincter.

While various injectable formulations of biologics are envisioned for use with the present invention, an injectable InteXen® solution can be employed in various embodiments. InteXen®, or InteXen™, is a non-chemically crosslinked porcine dermis that can provide a relatively soft, pliable biomaterial. Hydrated or non-hydrated InteXen® can be utilized. In this particular example, the InteXen® can be ground (e.g., LN2 grinding) into particles to generate a paste-like injectable solution. Various known grinding, sieving and like techniques can be employed to obtain the desired consistency or particle size for the injectable paste or solution. Further, various known needles (e.g., 20 g-22 g needles), devices and techniques can be implemented to inject or otherwise deliver the solution into targeted tissue of the patient. Channelized or uniform distribution of the solution within the tissue or organ of the patient may be better obtained if the solution is injected during needle withdrawal, thus avoiding solution accumulation or pooling. InteXen® is a biologic material (processed porcine dermis) that is manufactured by American Medical Systems, Inc. and sold as a graft material for surgical applications.

The injectable solution (e.g., InteXen®) can be loaded or otherwise provided with various drugs, hormones or steroids (e.g., estradiol), stem cells, growth factors and/or other bioactive agents. In one embodiment, the solution can be loaded with a basic fibroblast growth factor (b-FGF). Various saturations of particularized InteXen® with b-FGF can be employed as understood by those of ordinary skill in the art.

Figure 3:
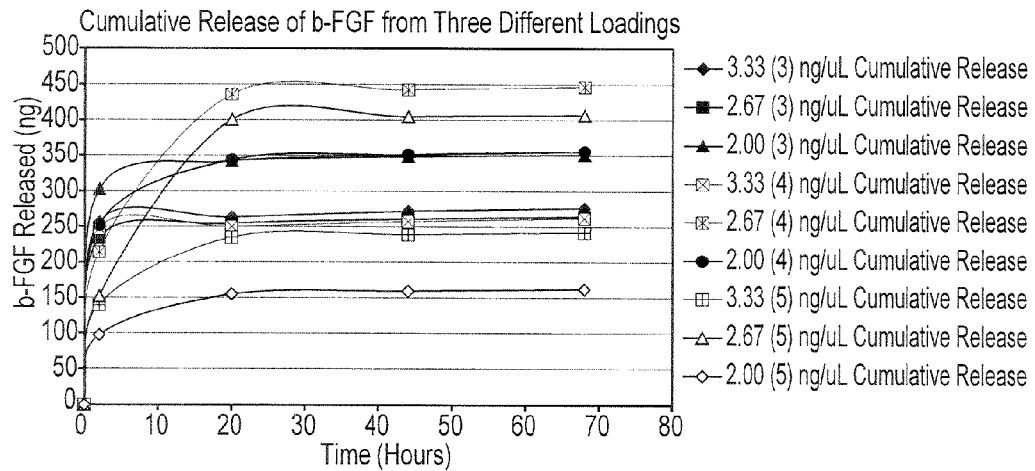
FIG. 3 graphically illustrates cumulative release of b-FGF from a particularized biologic at multiple loadings in accordance with embodiments of the present invention.
Figure 4:
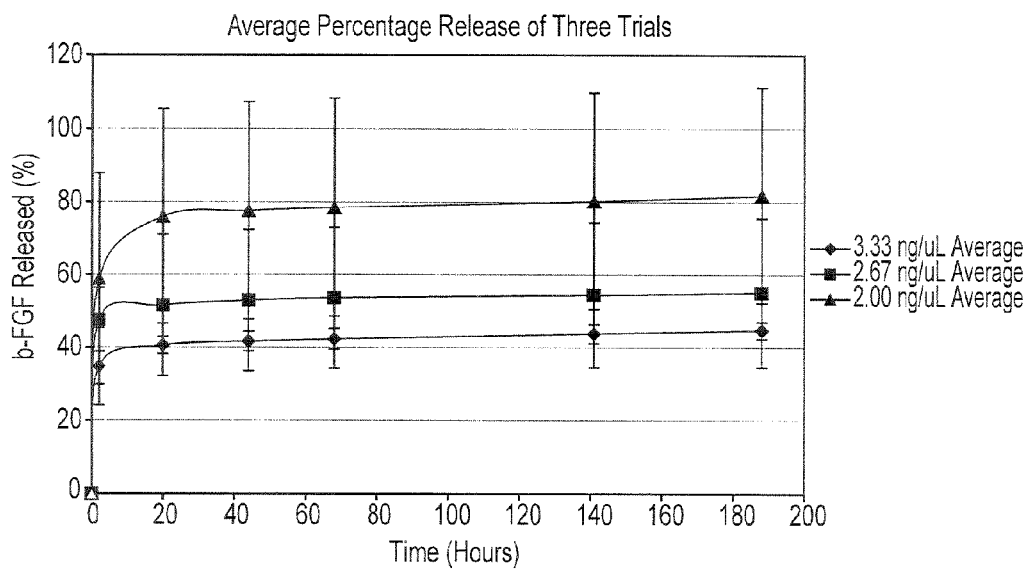
FIG. 4 graphically illustrates average percentage release of b-FGF from a particularized biologic in accordance with embodiments of the present invention.
Figure 5:
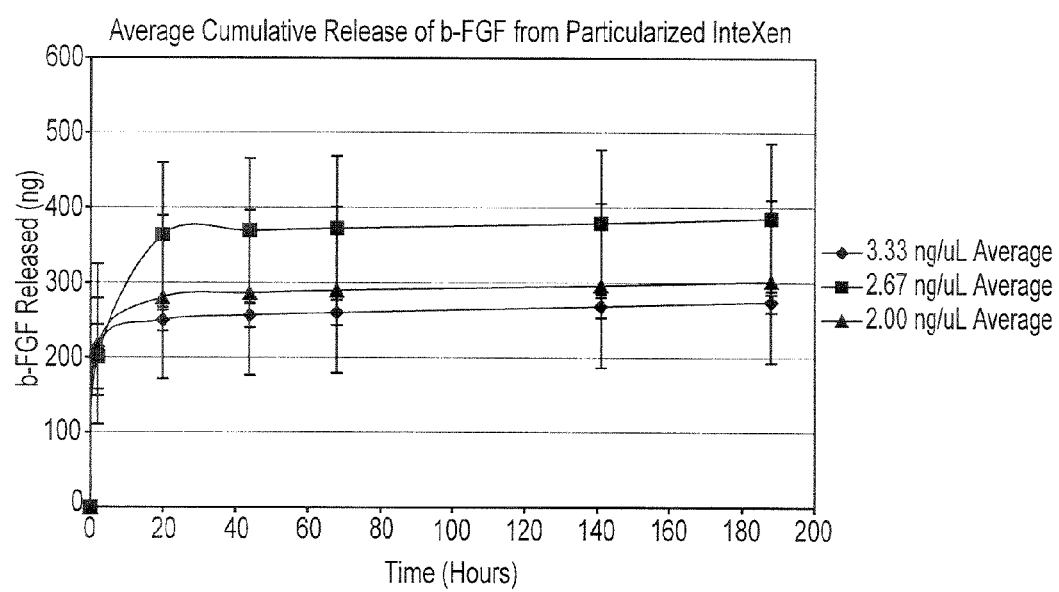
FIG. 5 graphically illustrates average cumulative release of b-FGF from a particularized biologic in accordance with embodiments of the present invention.

FIGS. 3-5 depict ELISA data for the release of the b-FGF from particularized InteXen® at various loadings.

In addition to those materials and agents expressly described, various and known biodegradable polymers, biologics, microspheres, gels, patches, proteins, steroids, porous materials, collagen, elastin, or biopolymers can be utilized with embodiments of the present invention to obtain the desired delivery and localized treatment benefits of the exemplary embodiments of the present invention.

In various embodiments, the biologic can be incorporated or otherwise provided with various implants, slings (e.g., mesh or thin sheets), or like devices to combine the benefits of the biologic formulation with devices adapted to support prolapse tissues/organs or otherwise treat incontinence (including but not limited to urinary, fecal and flatal incontinence). Other applications include, levator avulsion and muscle repair as well as repair of damaged tissue from prostectomy procedures. For instance, InteXen® (particularized or non-particularized) loaded with growth factors, steroids, stem cells or other agents can be incorporated with, coated or otherwise provided with known sling or implant and repair systems (e.g., for male and female), features and methods, including those disclosed in U.S. Pat. Nos. 7,500,945, 7,407,480, 7,351,197, 7,347,812, 7,303,525, 7,025,063, 6,691,711, 6,648,921, and 6,612,977, International Patent Publication Nos. WO 2010/027796, WO 2008/057261 and WO 2007/097994, and U.S. Patent Publication Nos. 2002/151762 and 2002/147382. Accordingly, the above-identified disclosures are fully incorporated herein by reference in their entirety.

All patents, patent applications, and publications cited herein are hereby incorporated by reference in their entirety as if individually incorporated, and include those references incorporated within the identified patents, patent applications and publications.

Obviously, numerous modifications and variations of the present invention are possible in light of the teachings herein. It is therefore to be understood that within the scope of the appended claims, the invention may be practiced other than as specifically described herein.

What is claimed is:

1. A biologic delivery system for treating pelvic disorders in a patient, comprising:
   a biologic that is a particularized non-chemically crosslinked porcine dermis loaded with a bioactive agent selected from the group consisting of a growth factor and a hormone;
   a pelvic implant device adapted to support pelvic tissue of the patient and to deliver the loaded bioactive agent to a target tissue within the pelvic region of the patient, wherein the pelvic implant device is a pelvic sling constructed at least in part of a mesh material or a thin sheet, and the biologic is incorporated into or coated on the pelvic sling.

2. The system of claim 1, wherein the bioactive agent includes a basic fibroblast growth factor.

3. The system of claim 1, wherein the bioactive agent includes a hormone.

4. The system of claim 3, wherein the hormone includes estrogen.

5. The system of claim 1, wherein the bioactive includes a protein.

6. The system of claim 1, wherein the pelvic implant device is a pelvic sling device constructed at least in part of a mesh material.

7. The system of claim 1 wherein the pelvic sling device is configured for the treatment of tissue or organ prolapse.

8. The system of claim 1 wherein the pelvic sling device is configured for the treatment of urinary incontinence.

9. A method of treating a pelvic disorder in a patient with a biologic delivery system, comprising:
providing the pelvic implant device of claim 1 to a pelvic area in a patient; and
allowing the device to support pelvic tissue of the patient and to deliver the loaded bioactive agent to target tissue at the pelvic area of the patient to treat the pelvic disorder.

10. The method of claim 9, wherein the bioactive agent includes a hormone.

11. The method of claim 9, wherein the bioactive agent includes a growth factor.

* * * * *